(12) United States Patent     (10) Patent No.: US 9,347,893 B2
Nelson et al.     (45) Date of Patent: May 24, 2016

(54) ENHANCED RESOLUTION IMAGING SYSTEMS FOR DIGITAL RADIOGRAPHY

(76) Inventors: Robert Sigurd Nelson, La Mesa, CA (US); William Bert Nelson, Excelsior, MN (US)

( * ) Notice: Subject to any disclaimer, the term of this patent is extended or adjusted under 35 U.S.C. 154(b) by 597 days.

(21) Appl. No.: 13/507,659

(22) Filed: Jul. 18, 2012

(65) Prior Publication Data

US 2013/0028379 A1     Jan. 31, 2013

Related U.S. Application Data

(60) Provisional application No. 61/572,957, filed on Jul. 26, 2011.

(51) Int. Cl.
*G01N 23/04* (2006.01)
*H01L 27/146* (2006.01)
*A61B 6/00* (2006.01)

(52) U.S. Cl.
CPC .......... *G01N 23/04* (2013.01); *H01L 27/14601* (2013.01); *A61B 6/484* (2013.01); *G01N 2223/50* (2013.01); *H01L 27/14658* (2013.01)

(58) Field of Classification Search
CPC ............. G21K 2207/005; A61B 6/484; H01L 27/14658; H01L 27/14601; G01T 1/16
USPC ........................................................... 378/62
See application file for complete search history.

(56) References Cited

U.S. PATENT DOCUMENTS

2009/0134334 A1*   5/2009   Nelson ..................... 250/361 R
2009/0238334 A1*   9/2009   Brahme et al. ................. 378/41
2010/0320391 A1*   12/2010   Antonuk ............. H01L 27/1462
                                                                                                                            250/366

* cited by examiner

*Primary Examiner* — Jack Berman
*Assistant Examiner* — Kevin Chung

(57) ABSTRACT

The invention provides methods and apparatus for enhanced PCI and dual-use radiation imaging systems. In one implementation high resolution storage phosphor plate radiation detector (an area detector) is employed for conventional attenuation radiation imaging and/or PCI (including conventional PCI and coded aperture PCI). Slit and slot scan implementations for dual-use systems are introduced. Dedicated single and dual-use slit and slot scan system for conventional attenuation imaging and PCI are described that employ face-on or edge-on detectors. Slit and slot scan systems that employ area detectors are described. Edge-on, structured cell detector designs are described. Applications of edge-on structured cell detectors for CT, Nuclear Medicine, PET, and probe detectors are described.

7 Claims, 8 Drawing Sheets

ENHANCED RESOLUTION IMAGING SYSTEMS FOR DIGITAL RADIOGRAPHY

This is a continuation of provisional application No. 61/572,957 filed on Jul. 26, 2011.

FIELD OF THE INVENTION

This invention provides novel enhanced resolution imaging systems and designs for use in digital radiography with applications for medical, industrial and scientific imaging.

BACKGROUND OF THE INVENTION

Conventional digital x-ray radiographic imaging systems record a representation of the attenuation that x-rays experience while traversing a medium. Detector options include integration, photon counting, and energy resolution capability in geometric configurations that include slit, slot, small area, and full field of view imaging formats. The development of effective image contrast enhancement techniques for digital radiography has taken various forms: optimizing the x-ray source emission spectrum, employing more efficient detectors and detector with photon counting or spectroscopy capability (Nelson, U.S. Pat. No. 4,937,4534), introducing contrast materials into the subject (for example, the human body), using analyzers (Nelson, U.S. Pat. No. 4,969,175) with coherent synchrotron sources (DEI) and using small (for example, a micro-focal spot) x-ray radiation source alone or in conjunction with a coded aperture to exploit phase contrast imaging (PCI). The contrast gains achieved with PCI typically improve as the source size decreases and/or the unshielded (active) detector pixel size decreases. PCI limitations typically include reduced tube output as focal spot size decreases and reduced detection efficiency if the active pixel area is reduced. The benefits of PCI imaging compared to attenuation imaging tend to be more pronounced for imaging of small structures or nonuniformities within an object. Hence, x-ray radiation detectors that offer high spatial resolution are typically employed. PCI images, as with conventional digital x-ray images, suffer from the effects of attenuation (absorption, scattering) and variable magnification for a thick object, as well as from the effects of overlapping structures and nonuniformities in the object. An object such as a breast with a complex tissue structure may represent a challenge in that the contrast gains derived from PCI may also generate unexpected artifacts. There are other sources that may contribute to image (signal) degradation that tend to be present in x-ray radiographic imaging systems. Radiation crosstalk effects between detector elements and radiation loss effects from detector elements (due to scattered x-rays, characteristic x-rays, bremsstrahlung x-rays, Compton electrons and photoelectrons, and optical photons if applicable) as well as detector element electronic noise and electronic crosstalk effects between detector elements can effect the final image quality. Conventional digital x-ray radiography dominates the medical, industrial, and scientific markets at this time with the expectation that PCI systems may be competitive in the future for specific applications. A commercial clinical mammography (mask-less) PCI system (see Morita T, et al., Lecture Notes in Computer Science, 5116, p. 48-54, 2008) with a microfocal spot x-ray tube source (approximately 100 micron focal spot size) that employs magnification (which contributes to scatter reduction) has experienced limited success due to the modest improvements obtained in contrast enhancement of small structures. A smaller focal spot improves contrast enhancement but at the cost of longer exposure times (creating a concern for patient motion issues). PCI devices (see Oliva A, et al., Nucl. Instru. Meth. A, vol. 610, p. 604-614, 2009; Munro P, et al., Phys. Med. Biol., vol. 55, p. 4169-4185, 2010; Keyrilainen J, et al., Acta Radiologica vol. 8, p. 866-884, 2010) with coded apertures (which also use magnification) that are currently undergoing development deploy pre-object and pre-detector masks. The pre-object mask creates microbeams wherein each microbeam illuminates a fraction of each detector element or pixel in a linear array (1-D) or a single detector element (2-D). The pre-detector mask (shading a fraction of each detector element and/or the region between detector elements from incident radiation). Alignment of pre-object and pre-detector masks with an array of discrete detector elements is challenging. Rigid pre-object and pre-detector masks (apertures) are typically designed with a "fill-factor" which represents the fraction of the aperture that is open to transmit radiation. If the fill-factor is zero then dark field images can be acquired. The illuminated detector element or pixel fraction can be varied by changing the relative position (overlap) of one mask with respect to the other. High spatial resolution detectors are particularly useful since the problem of "spill over" of a pixel signal into adjacent pixels can be reduced for a particular imaging application. Preferably, the pre-detector mask is positioned close to the detector and the mask materials heavily attenuate the incident radiation (using x-ray radiation of a suitable spectrum along with one or more dense, moderate-to-high atomic number mask materials such as Cu, Ag, W, Pb, Au and U). There is a contrast benefit if individual microbeams overlap their corresponding detector masks (albeit with an increase in patient dose). If a fraction of the active area of a detector element is shaded from x-rays then this electronically-active fraction can contribute to the total detector element readout noise due to the radiation effects and sources of electronic noise mentioned previously. Focal spot sizes less than 100 microns have been tested with experimental 1-D and 2-D coded aperture PCI designs.

SUMMARY OF THE INVENTION

The invention utilizes available and new x-ray detector technology and systems to offer either improved PCI capabilities or dual use capabilities (combining capabilities for both PCI and conventional digital x-ray attenuation imaging). One such technology is the storage phosphor plate (or screen) x-ray detector. Storage phosphor plate technology (including nano-particle storage phosphor ceramic plates (uniform and fiber optic plates) capable of extremely high spatial resolution and good detection efficiency) is suitable for large area and small area medical imaging applications such as digital mammography, spot area (small area) digital mammography, digital tomosynthesis, and digital dentistry as well as industrial and scientific applications. Although storage phosphor plates have been used for conventional digital x-ray attenuation imaging they are also particularly well-suited for use with existing commercial PCI imaging systems and with future PCI systems based on coded apertures since the storage phosphor plate detector offers an essentially continuous detector (there are no detector pixel alignment issues with the pre-detector mask) and high spatial resolution capabilities along with good detection efficiency. Thus, by employing high resolution storage phosphor plate detectors enhanced PCI systems can be implemented. Since the storage phosphor plates (energy integrating detectors) are also suitable for conventional (attenuation) digital imaging systems (attenuation imaging) then dual-use imaging systems that combine conventional digital imaging system and PCI system capabilities can be constructed. Several implementations of an enhanced PCI system that uses a coded aperture can be assembled as stand-alone systems (or incorporated into dual-use systems). For example, in one implementation of an enhanced PCI system the 2-D pre-detector mask is positioned close to the storage phosphor plate detector during imaging but the plate can be removed (if necessary) and scanned without altering the alignment of the pre-object and pre-detector masks.

A dual-use imaging system can be implemented by enabling the mechanical removal of the aligned pre-object and pre-detector masks from the radiation beam path so that a conventional attenuation, digital image can be acquired. If the level of desired magnification for the conventional digital image is different from what is required for PCI acquisition then appropriate adjustments in the distances between the radiation source, object, and storage phosphor plate detector can be performed. If the radiation source size and/or energy spectral distribution requirements differ for conventional digital imaging and PCI acquisition modes then a selection of radiation sources and/or energy spectra are made available. Therefore, more than one distinct radiation source can be incorporated into the dual-use imaging system if needed. A second implementation of the dual-use imaging system involves the bonding of the 2-D pre-detector mask directly to one face of the storage phosphor plate, permitting conventional digital x-ray imaging using one face and PCI from the opposite face of the storage phosphor plate. A third implementation of a dual-use imaging system positions two storage phosphor plates such that the front plate intercepts the radiation beam before it reaches the rear plate. A conventional digital image and a PCI can be acquired at the same time if a pre-detector mask is located between the front and rear storage phosphor plates. The pattern of the pre-object mask will be imposed on the front storage phosphor plate (which stores the conventional digital image). The front storage phosphor plate thickness should be adjusted so that both front and rear storage phosphor plates receive adequate radiation exposure. A variation of the two storage phosphor plate design is to enable dual energy imaging by (optionally) remove the pre-object mask (if present) and the pre-detector mask from the radiation beam path and inserting additional material filtration (if appropriate) between the two storage phosphor plates prior to image acquisition. Furthermore, 2-D array detectors can be used in place of storage phosphor plates in the dual-use imaging systems.

The storage phosphor plate detector elements are defined by the optical readout beam which allows various optical scanning options to be employed. One option is to scan only the active detector regions and ignore the shaded detector regions and thereby create a single, active PCI image. A second option is to form two images by scanning both the active detector regions and the shaded detector regions. A third option is to scan either the active regions alone or both of the active and shaded regions on a fine spatial element level (sub-region scanning). Sub-region scanning may provide greater detail about the PCI effect. Although the use of discrete 2-D array detectors is more demanding in terms of pre-detector mask alignment, nonetheless the same dual use capability can still be implemented. Bonding the pre-detector mask to the 2-D array detector for dual-use imaging (comparable to bonding a pre-detector mask on a storage phosphor plate) may be acceptable if front-side or back-side irradiation of the 2-D detector is acceptable. Potential radiation detector types include, but are not limited to, gases, scintillators, semiconductors, amorphous semiconductors and structured detectors. One promising structured radiation detector (a structured cell radiation detector) is based on quantum dots embedded in a material such as porous (or etched) silicon. Conventional discrete 2-D detector arrays are typically employed as x-ray integrator but specific implementations may offer photon counting or spectroscopic (energy resolution) capability (albeit at greater expense). In particular, for small area detectors the cost of implementing photon counting or spectroscopy capabilities is much more reasonable. Although flat plate (or flat surface) detector geometries are common, curved plate (or curved surface) detectors can also be employed for single use PCI or dual use imaging. Suitable changes must be implemented to the surfaces of pre-object and pre-detector masks in order to project properly onto the curved detector plate.

Small area imaging applications such as spot mammography may be implemented using a small focal spot source along with several options for coded aperture use. Either employ pre-subject and pre-detector masks or no masks at all. For a small area imaging application such as oral dentistry a pre-object mask and the pre-detector mask can be packaged into a rigid frame such that the detector and pre-detector mask fit inside the mouth while the aligned pre-object mask is located outside the mouth. The package can then be aligned by optical or mechanical means with the small focal spot of the radiation source. The advantage of magnification is lost since the detector is close to the object being imaged. Oral dentistry imaging with PCI capability can be implemented with digital cameras detectors and storage phosphor plate (or screen) detectors as well as structured radiation detectors.

The invention provides dual-use capabilities for digital slit scanning, slot scanning and CT scanning systems. An attenuation image can be acquired, a PCI image can be acquired, or both can be acquired using a dual imaging system using any of these scanning formats. One option is to acquire a full image of the object with one imaging technique and then acquire a small image of a questionable region of the object using the other imaging technique (the same or different radiation beam energy spectrum and radiation beam size may be employed) for additional information. For high resolution slit scanning a small focal spot source can be used alone or be combined with 1-D pre-object and pre-detector masks which can be moved into or out of the x-ray beam path based on the image requirements. Furthermore, an adjustment of the slits such that the projection of the x-ray beam from the pre-object slit overlaps the pre-detector slit can be used to extend the PCI effect from 1-D to 2-D. A 1-D PCI effect can be implemented with only the slits by adjusting the slits such that the radiation beam from the pre-object slit slightly overlaps the pre-detector slit to enable a 1-D PCI effect. The radiation source-detector distance can be altered to achieve the desired level of magnification for PCI. Slot scanning can employ movable 2-D pre-object and pre-detector masks that incorporate a selection of aperture dimensions that can be used to tune the PCI effect as needed. Multiple sets of slits or slots can be employed to increase radiation source utilization efficiency. The slit detector linear array geometry with respect to the x-ray beam can be face-on, edge-on, or near-edge-on (tilted edge-on). In those implementations in which either edge-on or near-edge-on (tilted edge-on) detector geometries are acceptable the detector geometry will simply be referred to as edge-on. The choice of detector may depend on the x-ray source(s) and operational energy spectrum(s) employed. A face-on or edge-on gas, scintillator, semiconductor or structured detector may be suitable if it offers adequate spatial resolution and detection efficiency along with appropriate integration or photon counting or energy resolution capability. Structured detectors include structured cell detectors (which typically incorporate materials such as semiconductor quantum dots or an amorphous semiconductor or polycrystalline semiconductor) as well as detectors such as 3-D semiconductor detectors (see Da Via C, Nucl. Instru. Meth. A, vol. 594, p. 7-12, 2008). In some applications an edge-on Detector geometry may be preferred to a face-on detector geometry for a particular type of detector. The detection efficiency of a thin, structured detector (structured cell or 3-D semiconductor detectors) in a face-on geometry increases significantly when positioned edge-on (making it desirable for both conventional attenuation digital imaging slit scanning and PCI slit scanning). For example, a structured cell quantum dot detector might offer inadequate detection efficiency in a face-on detector geometry for a specific imaging application. With an edge-on detector geometry the useful active detector thickness depends on the width of the detector which can range from less than one millimeter to multiple millimeters or even centimeters. In addition to any energy resolution capability due to the readout electronics limited energy resolution is also offered as a result of x-ray beam hardening. Furthermore the x-ray count rate per detector element can be reduced by spreading the detection process over multiple detector elements. A potential benefit from the edge-on geometry is that the cell depth does not need to be much larger than the slit width (slit opening) in the scan direction. The choice of cell geometric distributions ranges from uniform patterns to patterns such as honey combs or offset patterns (offset between successive rows, for example) to nonuniform patterns. The usefulness of various cell shapes for face-on and edge-on detectors may depend on how cell dimensions and manufacturing costs impact detection efficiency. Standard shell shapes such as circles, squares, hexagons, etc. as well as new cell shapes such a trenches, can be implemented. Standard readout systems already in use with structured cell quantum dot x-ray detectors as well as other radiation detectors (such as flat panel arrays or semiconductors bonded to ASICs, etc.) can be employed based on speed, signal quality and cost requirements. As was mentioned earlier, capabilities such as photon counting and energy resolution as well as depth-of-interaction (DOI) resolution with pixel sizes that are fixed or vary with depth (based on the incident energy spectrum and any need to distribute a high count rate between multiple pixels) can also be implemented (see Nelson R, U.S. Pat. No. 4,560,882, Dec. 24, 1985; Nelson R, U.S. Pat. No. 4,937,453, Jun. 26, 1990; Nelson R, U.S. Pat. No. 6,583,420, Jun. 24, 2003; Nelson R, U.S. Pat. No. 7,291,841, Nov. 6, 2007; Nelson R, U.S. Pat. No. 7,635,848, Dec. 22, 2009 and Divisional U.S. Pat. No. 8,115,174 B2, Feb. 14, 2012, Divisional U.S. Pat. No. 8,115,175 B2, Feb. 14, 2012, Divisional U.S. Pat. No. 8,183,533 B2, May. 22, 2012; Nelson R, U.S. Pat. No. 8,017,906, Sep. 13, 2011). Additional capabilities such as temperature control, power control, signal processing and communications and storage are incorporated into the detector package. The edge-on, structured detector represents an alternative to edge-on scintillator detectors and edge-on semiconductor detectors. Existing readout systems and features can be employed with the structured detector. Although the readout elements (typically the anodes) used in face-on and edge-on slit scanning can be uniform and parallel it is relative straightforward to form a readout geometry that diverges from the radiation entrance surface to compensate for the (typical) diverging nature of most x-ray sources. In those instances in which the radiation beam divergence is gradual then employing focused, rectangular readout strips that follow the divergence may be an acceptable substitute for focused, diverging readout strips. Furthermore, although the entrance surface of the detector is typically flat it can be contoured if an application benefits significantly from this modification.

The edge-on, structured detectors previously described (as well as other versions) are also suitable for human and small animal Nuclear medicine imaging (including probes) and PET imaging since they offer high spatial resolution, good timing resolution, and good energy resolution. Reduced readout costs can be attained (usually with some reduction in signal quality) by implementing weighted readouts based on contributions from the detected signals of one or multiple detector elements shared between two readout elements for at the ends of an 1-D detector or four readout elements at the corners of a 2-D detector (see Nelson R, U.S. Pat. No. 8,115, 175 B2, Feb. 14, 2012).

Although attenuation and PCI slit and slot scanning have been described in conjunction with dedicated detectors the same techniques can be applied to 2-D storage phosphor plate detectors and other conventional 2-D array detectors. The advantage of inherent scatter reduction is available in both modes for these 2-D detectors. Multiple sets of slits or slots can be employed to increase x-ray source utilization efficiency.

The details of one or more embodiments of the invention are set forth in the accompanying drawings and the description below. Other features, objects, and advantages of the invention will be apparent from the description and drawings, and from the claims.

All publications, patents and patent applications cited herein are hereby expressly incorporated by reference for all purposes.

DETAILED DESCRIPTION

Figure 1:
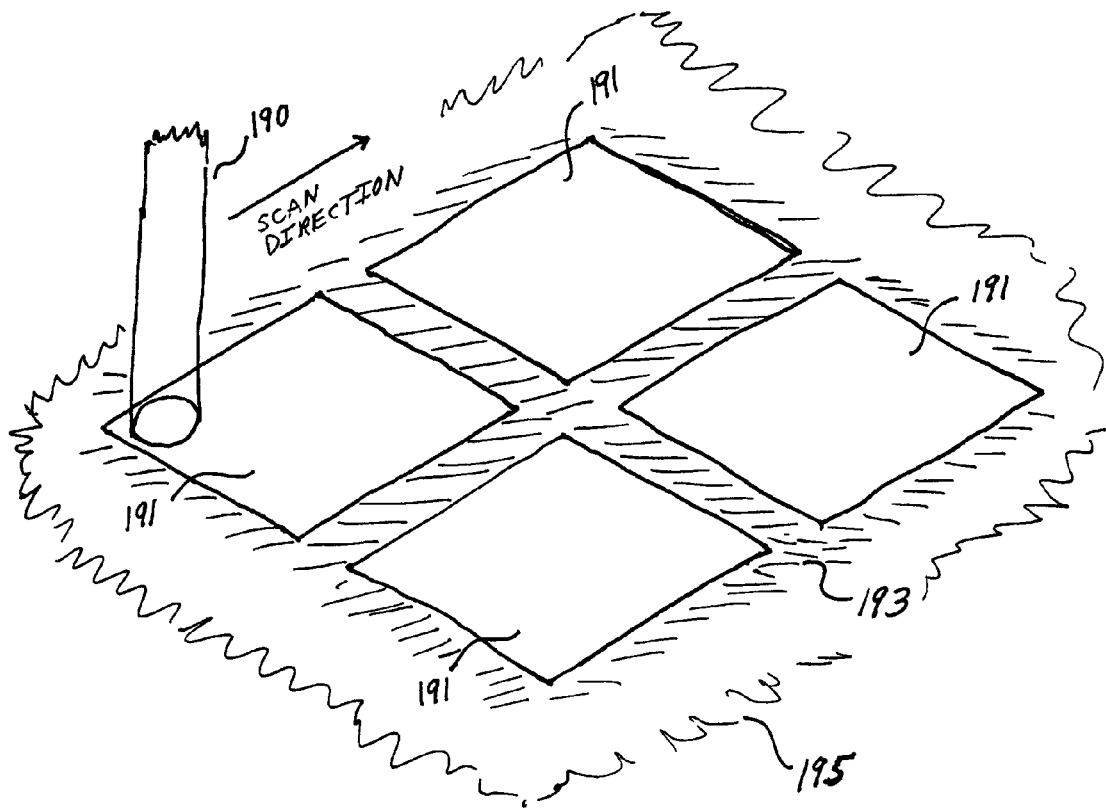
FIG. 1 illustrates a perspective view of an optical beam scanning sub-regions of active and shadowed regions of an exposed storage phosphor plate.

The invention utilizes existing and new x-ray detector technology and systems to offer either improved PCI capabilities or dual use capabilities (combining capabilities for both PCI and conventional (attenuation) digital x-ray attenuation imaging). One such technology is the storage phosphor plate (or screen) x-ray detector. Storage phosphor plate technology (including nano-particle storage phosphor ceramic plates (uniform and fiber optic plates) capable of extremely high spatial resolution) is suitable for large area and small area medical imaging applications such as digital mammography (see Rowlands J, Phys. Med. Biol., vol. 47, R123-R166, 2002; Johnson J, et al., J. Am. Ceram. Soc. Vol. 90, no. 3, p. 693-698, 2007), spot area (small area) digital mammography, digital tomosynthesis, and digital dentistry (as described in Nelson, U.S. patent application Ser. No. 12/930,771, Jan. 18, 2011 and incorporated herein) as well as industrial and scientific applications. For some applications like digital mammography and digital dentistry multiple sizes of storage phosphor plates may be employed. A high resolution optical readout scanner is incorporated into the detector system and an electronic communications link to a computer for data post-processing, storage, and display is included. Although storage phosphor plates have been used for conventional digital x-ray attenuation imaging they are also particularly well-suited for use with current commercial PCI imaging systems and with future PCI systems that employ coded apertures due to the continuous nature of the active detector volume (there are no alignment issues as with an array of discrete detector element) and high spatial and contrast resolution capabilities. Thus, by employing high resolution storage phosphor plates enhanced PCI systems can be implemented. Storage phosphor plates are suitable for dedicate conventional digital imaging systems and dedicated PCI systems. (It will be shown that storage phosphor plate detectors are also suitable for dual-use imaging systems that combine conventional digital imaging system and PCI system capabilities.) In one implementation of an enhanced coded aperture PCI system the 2-D pre-detector mask overlaps the storage phosphor plate detector during imaging but remains independent of the plate so that the plate can be removed (if necessary) and scanned without altering the alignment of the pre-object and pre-detector masks. Options include mechanically moving the storage phosphor plate to a separate readout system or integrating the readout system with the storage phosphor plate. More than one storage phosphor plate can be incorporated into a PCI system or a dual-use imaging system to facilitate throughput.

A dual-use imaging system offers the flexibility of employing either a PCI or attenuation imaging mode if one of the imaging modes produces (or is expected to produce) unsatisfactory results. Furthermore, in some instances the two imaging modes will produce complementary results that will enhance analysis. A dual-use imaging system can be implemented by moving the aligned pre-object and pre-detector masks out of the path of the radiation source so that a conventional digital attenuation image can be acquired. If the level of desired magnification is different from the PCI acquisition mode then appropriate adjustments in the distances between the radiation source, object, and storage phosphor plate detector can be performed. If the radiation source size or spectral distribution is not suitable for both conventional digital imaging and PCI then a selection of radiation sources (multiple radiation sources) are offered. For example, a radiation source such as a diagnostic x-ray tube could offer a selection of focal spot sizes in addition to a selection of voltage settings so that it functions as multiple radiation sources contained within a single device. An alternative is to incorporate more than one distinct radiation source device into the dual-use imaging system. In addition to any scatter reduction achieved through magnification an optional anti-scatter grid or sets of moving slits or moving slots can be employed to further reduce the level of radiation scatter reaching the storage phosphor plate detector. If the projection of the radiation beam (such as an x-ray beam) from the pre-object slit is allowed to overlap the pre-detector slit then a 1-D PCI effect is enabled. This can be combined with 1-D pre-object and pre-detector masks to enable a 2-D PCI effect. In another implementation of the dual-use imaging system the 2-D pre-detector mask is directly bonded to one face of the storage phosphor plate, permitting conventional digital x-ray imaging from one face and PCI from the opposite face of the storage phosphor plate. The desired side of the plate can be positioned into the radiation beam path by mechanically translating and rotating the plate or by rotating the plate in place (if space permits). An alternative to using a single storage phosphor plate detector is to use a storage phosphor plate detector and a pre-detector mask bonded to a storage phosphor plate detector (each of which may be optimized for its respective imaging modes) at different times in a dual-use system. In yet another implementation of a dual-use imaging system two storage phosphor plates are oriented in parallel such that one plate (the front plate) intercepts the radiation beam before it reaches the second plate (the rear plate). This is an example of dual-mode image acquisition. A conventional digital image and a coded aperture PCI can be acquired at the same time if the pre-detector mask is located between the front plate and rear plate (as mentioned, an option is to bond the pre-detector mask to the rear plate). The radiation beam pattern of the pre-object mask is imposed on the conventional digital image. The thickness of the front plate can be optimized such that both front and rear storage phosphor plates form useful images while being irradiated. Furthermore, if two storage phosphor plates are imaged simultaneously then dual energy imaging can be implemented by removing (optionally) the pre-object mask and pre-detector mask from the radiation beam path and inserting additional material filtration (if needed) between the two plates prior to image acquisition. This is another type of dual-mode image acquisition. In general, 2-D array detectors can be used in place of storage phosphor plates in the dual-use imaging systems. They offer fast readout capability (usually at an increased cost).

Figure 2:
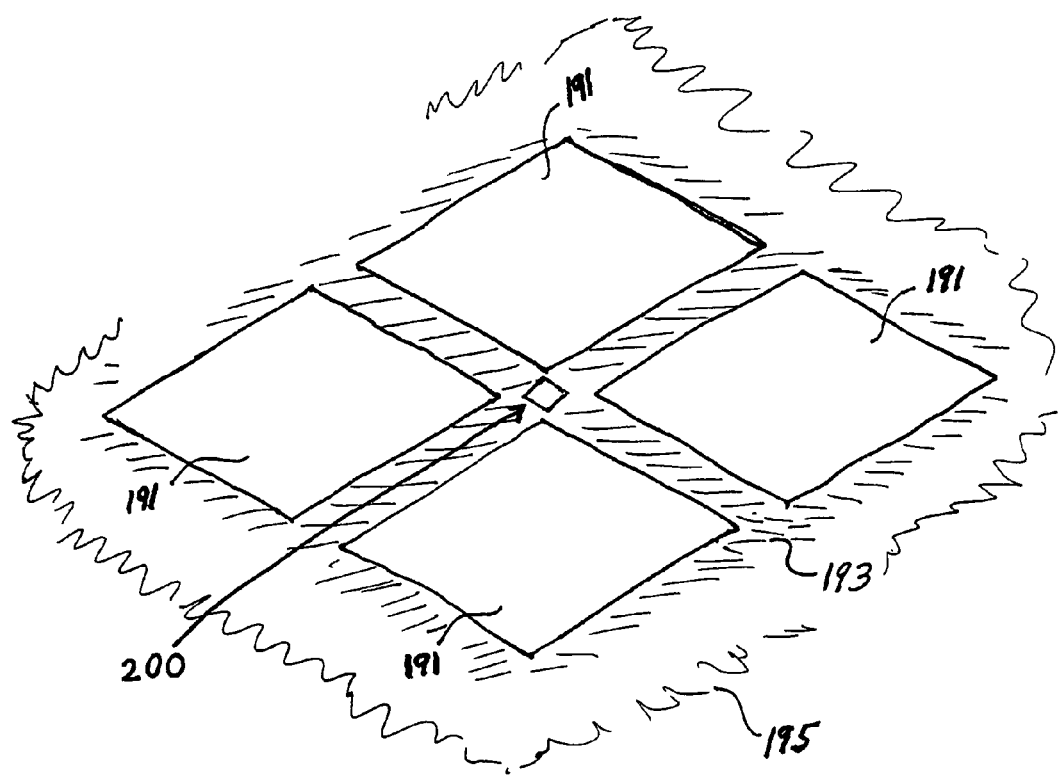
FIG. 2 illustrates a perspective view of a modified pattern for pre-object and pre-detector masks.

Since the storage phosphor plate detector elements are defined by the dimensions of the optical readout beam several optical scanning options are available. One option is to scan only the active detector regions and ignore the shaded detector regions and thereby create a single, active PCI image. Another option is to form two images by scanning both the active detector regions that comprise the active PCI image and the shaded detector regions (or the sub-region(s) of the shaded detector region near the detector mask boundary) that comprise the shaded PCI image. Yet another option is to implement sub-region scanning on either the active regions alone or both the active and shaded regions. Sub-region analysis may provide details about the structure of PCI effects on one or both sides of the detector mask boundary. Sub-region scan data can be selectively assembled to form larger image pixels of desired shapes (improving signal statistics per pixel). FIG. 1 shows a perspective view of an optical beam 190 scanning sub-regions of active detector regions 191 and shadowed detector regions 193 of an exposed storage phosphor plate 195. FIG. 2 shows a perspective view of modified pattern 200 for pre-object and pre-detector masks. Although a degree of flexibility is lost with the use of discrete 2-D array detectors in terms of the need for pre-detector mask alignment with the discrete detector pixels, the same dual-use capability can still be implemented. Bonding the pre-detector mask to the 2-D array detector for dual-use imaging (comparable to bonding a pre-detector mask on a storage phosphor plate) may be acceptable if front-side or back-side irradiation of the 2-D detector is acceptable. Mechanical manipulation of the 2-D array detector is required for positioning the desired side of the detector to intercept the radiation beam. A non-exclusive list of types of detector includes the well-known semiconductors (as well as amorphous and polycrystalline implementations) such as, but not limited to, silicon, germanium, diamond. selenium, CZT, CdTe, GaAs, PbO, $HgI_2$, $PbI_2$ detectors, structured detectors such as structured cell quantum dots (see Campbell I, Advanced Materials vol. 18 (1), p. 77-79, 2006; Urdaneta M, 2010 International Workshop on Radiation Imaging Detectors; Urdaneta M, 2010 IEEE Nuclear Science Symposium.) and 3-D semiconductor (such as silicon) detectors, gas detectors and scintillator detectors. Conventional, discrete 2-D detector arrays are typically employed as x-ray integrators but they can also be used as photon counters or for spectroscopy (albeit at greater expense). In particular, for small area detectors the cost of implementing photon counting or spectroscopy capabilities is much more reasonable. The spectroscopy capability can be used to enhance contrast for both attenuation imaging and PCI. An additional benefit of using spectroscopy in PCI is the ability to discriminate against the beam-hardened radiation that penetrates through the detector mask and is subsequently detected. This beam-hardened contribution to the PCI over a range of energy bins can be corrected for by a calibration procedure. Thus, any one of these three detector modes may be employed if it is found to be cost-effective. Although flat plate detector geometries are widely implemented curved plate detectors can also be employed for PCI and dual-use imaging. Suitable changes must be implemented to the surfaces of pre-object and pre-detector masks in order for the radiation source to project properly onto the curved plate detector.

Certain small area imaging applications such as spot mammography may be implemented using a small focal spot source along with several options for coded aperture PCI use. Employ pre-subject and pre-detector masks or no masks at all (mask-less PCI). A storage phosphor plate detector or 2-D array detector may be employed. For example, in mammography, if compression of the breast is employed then a greater degree of compression can be utilized for a small area (reducing variations in magnification as well as the thickness of tissue in the x-ray radiation beam path). A small area imaging application such as oral dentistry is challenging since the detector must fit into the mouth. A pre-object mask and the pre-detector mask can be packaged into a rigid frame such that the detector and pre-detector mask fit inside the mouth and the aligned pre-object mask is located outside the mouth. A replaceable plastic bag can cover the detector and pre-detector mask combination while they reside in the mouth. The package is aligned by optical or mechanical means with the small focal spot of the radiation source. The advantage of magnification is lost since the detector is close to the object being imaged. Oral dentistry imaging with PCI capability can be implemented with digital cameras detectors and storage phosphor plate (or screen) detectors or other suitable digital detectors. The pre-detector mask can be bonded to the detector. Small area imaging with PCI capability can, in general, be implemented with a variety of detectors. A list of viable detectors for small area imaging includes, but is not limited to, digital camera detectors using scintillators or semiconductor, structured cell detector and storage phosphor plate (or screen) detectors (see Nelson R, U.S. patent application Ser. No. 12/930,771, filing date: Jan. 18, 2011). Dual-use imaging systems can be implemented for small area imaging applications.

Figure 3:
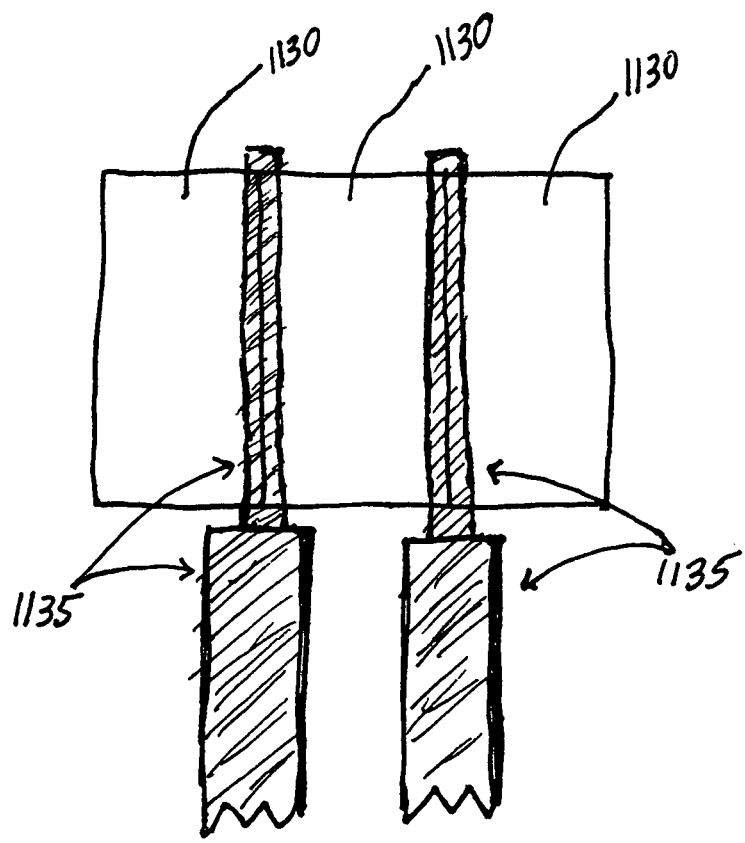
FIG. 3 illustrates a perspective view of a movable, variable pre-detector mask (or pre-object mask) that overlaps the boundary between two adjacent detector elements.

The invention provides dual-use capabilities for conventional digital slit and slot scanning systems. An electronic communications link is provided from the detector to a computer for data post-processing, storage, and display. Sets of slits (or slots) are employed to reduce detected scatter levels and minimize unnecessary radiation to the object. One slit or slot (the pre-object slit or slot) collimates the radiation beam prior to the object. The second slit or slot the pre-detector slit or slot) collimates the radiation beam prior to the detector. A PCI slit (slot) scan image can be acquired. A dual-use imaging system permits acquisition of a digital attenuation slit (slot) scan image or a PCI slit (slot) scan image, or both types of images. Preferably both imaging modes can be implemented using the same sets of slits (slots) and detectors. A more expensive alternative is to use separate sets of slit (slots) and detectors (and possibly separate radiation sources) for the two imaging modes. A motivation to deploy such as system is the need for different detector systems for the two imaging modes. Another implementation of this format is to permit acquisition of both the attenuation image and PCI at the same time if a dual scan is commenced, reducing motion artifacts in the two images. The radiation beam intensities Used for the two imaging modes need to be managed so that the attenuation image and the PCI are both of acceptable quality. Detectors with a wide dynamic range or photon counting or spectroscopy capability help to simplify this issue. For a dedicated coded aperture PCI slit scan device the coded aperture masks can be fixed, although the pre-detector mask can be design to be movable and variable (as explained below). Another implementation is to acquire a full image of the object with one technique and then acquire a second full image with the other technique. One option is to acquire a full image of the object with one imaging technique and then acquire small images of regions of interest of the object using the other imaging technique for additional information. The acquisition of attenuation and PCI images may require the use of different radiation beam energy spectrum and/or a different radiation beam size. The coded aperture pre-object and pre-detector masks can be mechanically moved out of the radiation beam path as needed. For high resolution slit scanning (for example, as currently employed for commercial digital slit scan mammography) a small focal spot source can be used alone or be combined with movable 1-D pre-object and pre-detector masks which can be moved into or out of the x-ray beam path based on the image requirements. Furthermore, these 1-D pre-object and pre-detector masks can be implemented as variable 1-D masks, offering flexibility in that these pre-object and pre-detector masks can each incorporate a selection of widths that can be used to tune the PCI effect as needed. FIG. 3 shows a perspective view of a movable, variable pre-detector mask 1135 that overlaps the boundary between adjacent detector elements 1130. A variable pre-object mask is of a similar design. Furthermore, an adjustment of the slits such that the projection of the x-ray beam from the pre-object slit overlaps the pre-detector slit can be used to extend the PCI effect from 1-D to 2-D. The slit edge will form one side of an equivalent 2-D PCI aperture (Munro P. et al., Phys. Med. Biol., vol. 55, p. 4169-4185, 2010) while the variable pre-object and pre-detector masks overlap to create an L-shaped pattern. Yet another implementation is to remove the pre-object and pre-detector masks and adjust the slits such that the radiation beam from the projection of the pre-object slit overlaps the pre-detector slit to enable a 1-D PCI effect (Munro P. et al., Phys. Med. Biol., vol. 55, p.

Figure 7:
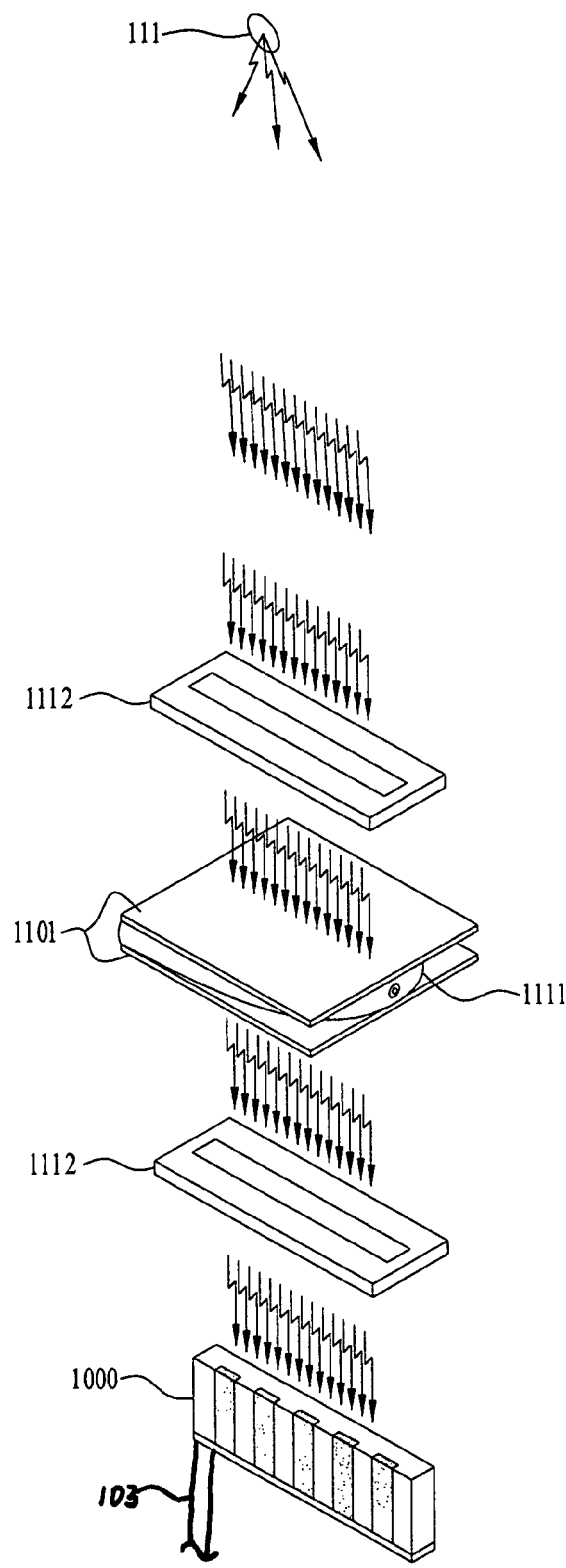
FIG. 7 illustrates a perspective view of a dual-use slit scan imaging system for PCI and conventional digital radiography imaging with a structured radiation detector positioned in an edge-on geometry.
Figure 8:
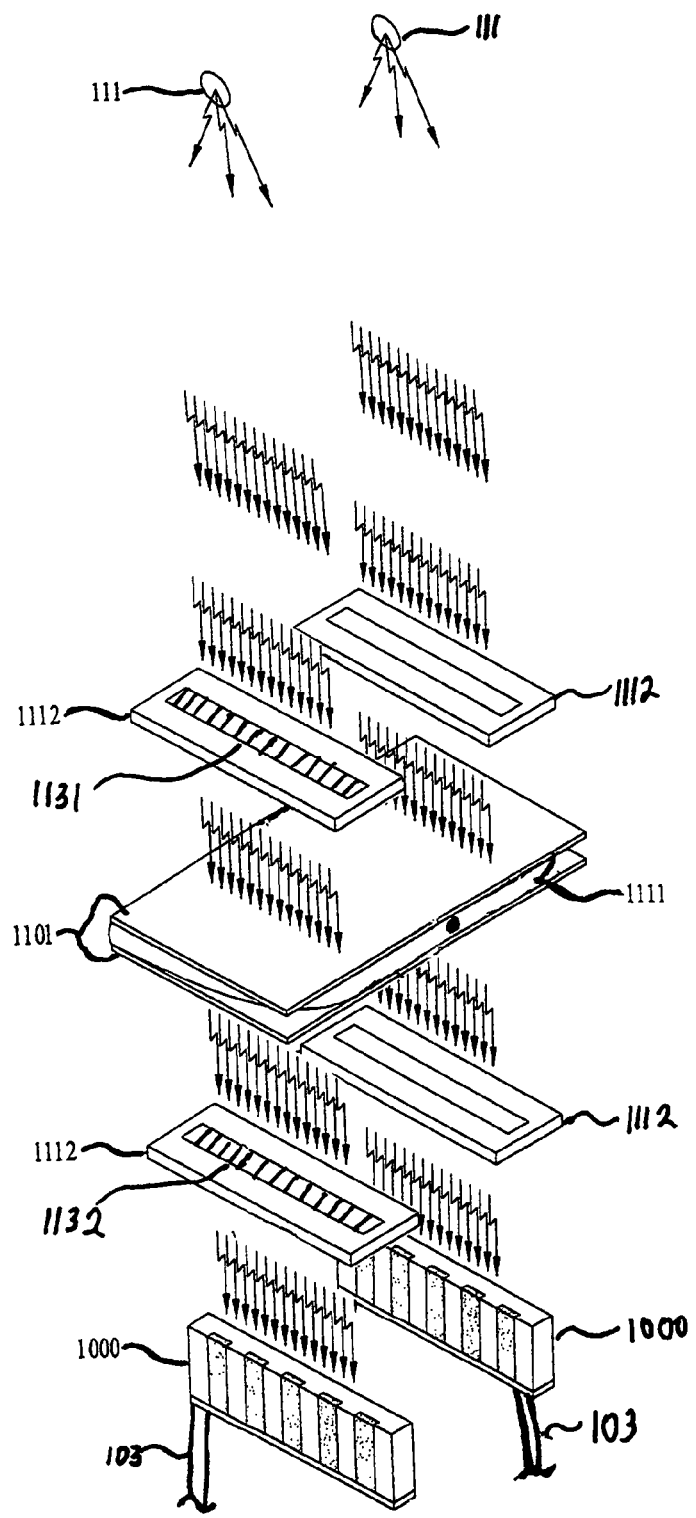
FIG. 8 illustrates a perspective view of a dual slit scan imaging system for simultaneous PCI and conventional digital radiography imaging with structured radiation detectors positioned in an edge-on geometry.

4169-4185, 2010). FIG. 7 shows a perspective view of a dual-use slit scan imaging system for PCI and conventional digital radiography imaging with a x-ray radiation source 111, pre-object and post-object slits 1112, a compressed object (breast) 1111 with compression plates 1101, an edge-on structured radiation detector 1000 and an electronic communications link to a computer 103. FIG. 8 shows a perspective view of one implementation of a dual slit scan imaging system for simultaneous PCI and conventional digital radiography imaging with x-ray radiation sources 111, pre-object and post-object slits 1112, pre-object mask 1131 and pre-detector mask 1132 for PCI, a compressed object (breast) 1111 with compression plates 1101, edge-on structured radiation detectors 1000 and electronic communications links to a computer 103. A dual imaging system for simultaneous PCI and conventional digital radiography imaging permits optimization of imaging parameters for each imaging system and good image registration between the PCI and the conventional image for analysis purposes. The dual imaging system with simultaneous acquisition is not limited to the use of only a specific PCI imaging system. Because a slit scanner with dedicated digital x-ray detectors uses a relatively small number of pixels compared to an area detector it can be cost-effective to design the detector array to offer sub-region scanning and analysis so that the directly illuminated fraction of the opening of the detector aperture is viewed by one detector pixel and the remaining fraction of the open aperture is covered by at least one additional detector pixel. Possible detector geometries include at least two rows of face-on pixel detectors or an edge-on linear array with sub-aperture resolution (SAR) per slit. The radiation source-detector distance can be altered to achieve the desired level of magnification for PCI. Slot scanning can employ movable 2-D pre-object and pre-detector masks that incorporate a selection of aperture dimensions that can be used to tune the PCI effect as needed. Multiple sets of slits or slots can be employed to increase radiation source utilization efficiency.

Figure 4:
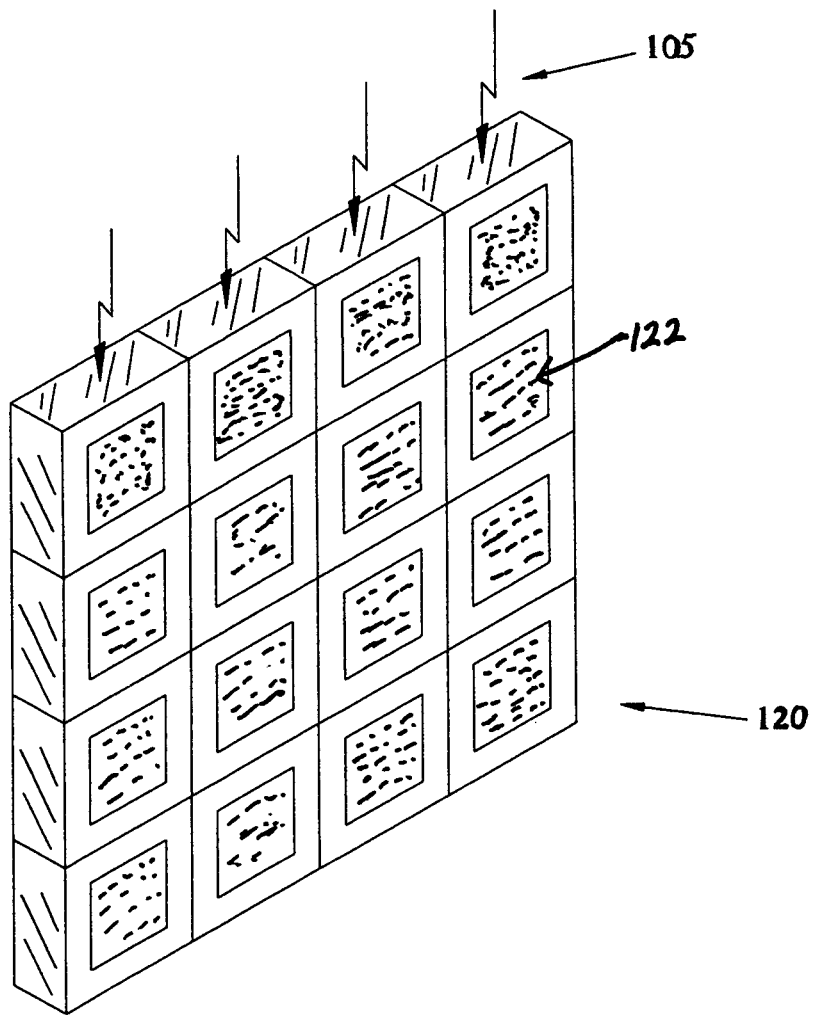
FIG. 4 illustrates a perspective view of a structured quantum dot detector with square cells positioned in an edge-on geometry appropriate for slit scan x-ray radiography.

The slit detector linear array geometry with respect to the radiation beam can be face-on, edge-on, or near-edge-on (tilted edge-on). Edge-on or near-edge-on (tilted edge-on) detector geometries are both referred to as edge-on detector geometries when it is understood that either can be employed. The choice of detector may depend on the x-ray source type and operating voltage (or voltages). Radiation sources other than x-ray tubes may be employed and more than one radiation source can be used in a system if appropriate. The preferred radiation source for attenuation imaging may be different from the preferred source for PCI. A face-on or edge-on gas, scintillator, semiconductor, amorphous semiconductor, polycrystalline semiconductor or structured detector (including 3-D semiconductor (such as silicon) detector or a structured cell detector which incorporates quantum dots or amorphous semiconductor or polycrystalline semiconductor materials) may be suitable if it offers adequate spatial resolution and detection efficiency (as well as appropriate integration or photon counting or energy resolution capability). If detection efficiency is inadequate or cost is excessive for a face-on detector geometry then an edge-on detector geometry may be preferable. For example, expensive (thick) silicon detectors in a face-on geometry are required for narrow slit scanning in x-ray mammography whereas relatively inexpensive (thin) silicon detectors in an edge-on geometry offer very high detection efficiency over the range of energies detected (Nelson R, U.S. Pat. No. 4,937,453, Jun. 26, 1990). The detection efficiency of relatively thin structured detector such as a structured cell quantum dot detector in a face-on geometry improves dramatically when positioned edge-on (making it suitable for both conventional digital slit scanning and PCI slit scanning). For example, a structured cell quantum dot detector comprised of PbS quantum dots embedded in porous or etched silicon cells (of various shapes including, but not limited to: circular, square, rectangular, hexagonal, triangular, elliptic and trench) with a typical depth of (but not limited to) 40-100 um might offer marginal detection efficiency in a face-on detector geometry for specific imaging application since the active detector thickness is comparable to the cell depth. However, in an edge-on geometry the active detector thickness depends on the width of the detector which can range from less than one mm to multiple mms or greater. In particular, an edge-on geometry that allows a reduced cell depth helps mitigate issues such as problems associated with non-uniform packing of quantum dots with increasing cell depth (resulting in non-uniform response issues in a face-on geometry and typically more expensive detectors due to poor manufacturing yields). Manufacturing yields may also improve if the active cell volume can be increased (for example, using a trench cell geometry) and thereby improving the packing uniformity of quantum dots. (The material used for the quantum dots is not limited to PbS. Furthermore, the materials that can be used to fill cells by growth or deposition are not limited to quantum dots. Amorphous or polycrystalline semiconductor materials which offer adequate energy bandgaps, electron and/or hole mobility, and stopping power may also be used with cells of appropriate size.) FIG. 4 illustrates a perspective view of x-ray radiation 105 incident on a structured cell quantum dot detector comprised of a uniform 2-D array of square cylindrical cells 120 positioned in an edge-on geometry appropriate for slit scan x-ray radiography. Each cell is packed with quantum dots 122. Although a uniform square cell geometry is shown in FIG. 4 other geometric distributions of cells (such as a honey comb patterns or offset patterns or nonuniform patterns) are straightforward to implement and may be helpful in mitigating detector aliasing effects or increasing detection efficiency. The usefulness of various cell shapes for face-on and edge-on detectors may depend on how cell dimensions and manufacturing costs impact detection efficiency. For example a circle cell shape may be less expensive than a square cell shape but generates more dead space (assuming the silicon material between cells has a low probability of interaction with the incident radiation) per unit area of detector material. Fewer cells may be need to provide some level of attenuation per unit length of detector material if elongated structures such as rectangular or elliptical cells shapes are employed. For face-on detection the likelihood of radiation interaction is primarily determined by the depth of the cell, its cross section shape (unless two or more detectors are stacked) and the cell density whereas for edge-on detection the depth of the cell, its cross section shape, the cell density and the number of cells in the radiation path are important. Standard readout systems already in use with structured cell quantum dot x-ray detectors as well as other radiation detectors (such as flat panel arrays or semiconductors bump bonded to ASICs, etc.) can be employed based on speed, signal quality and cost requirements. Features such as temperature, power control and signal processing as well as connections to a data acquisition and storage system such as a computer are assumed to be incorporated into the detector system package.

Figure 5:
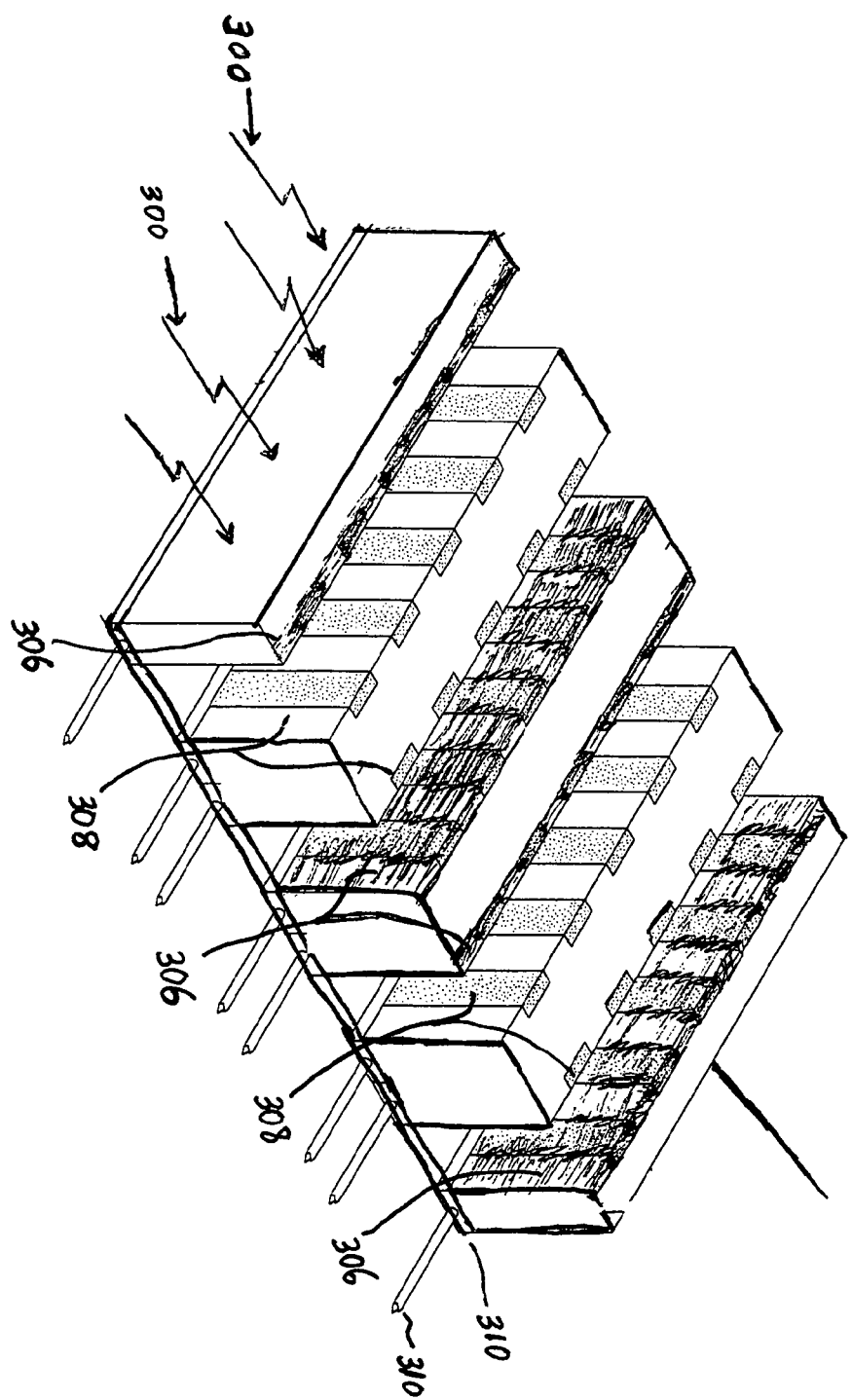
FIG. 5 illustrates a perspective view of a structured quantum dot detector with trench cells positioned in an edge-on geometry appropriate for slit scan x-ray radiography in which radiation is incident perpendicular to the long axis of the trench.
Figure 6:
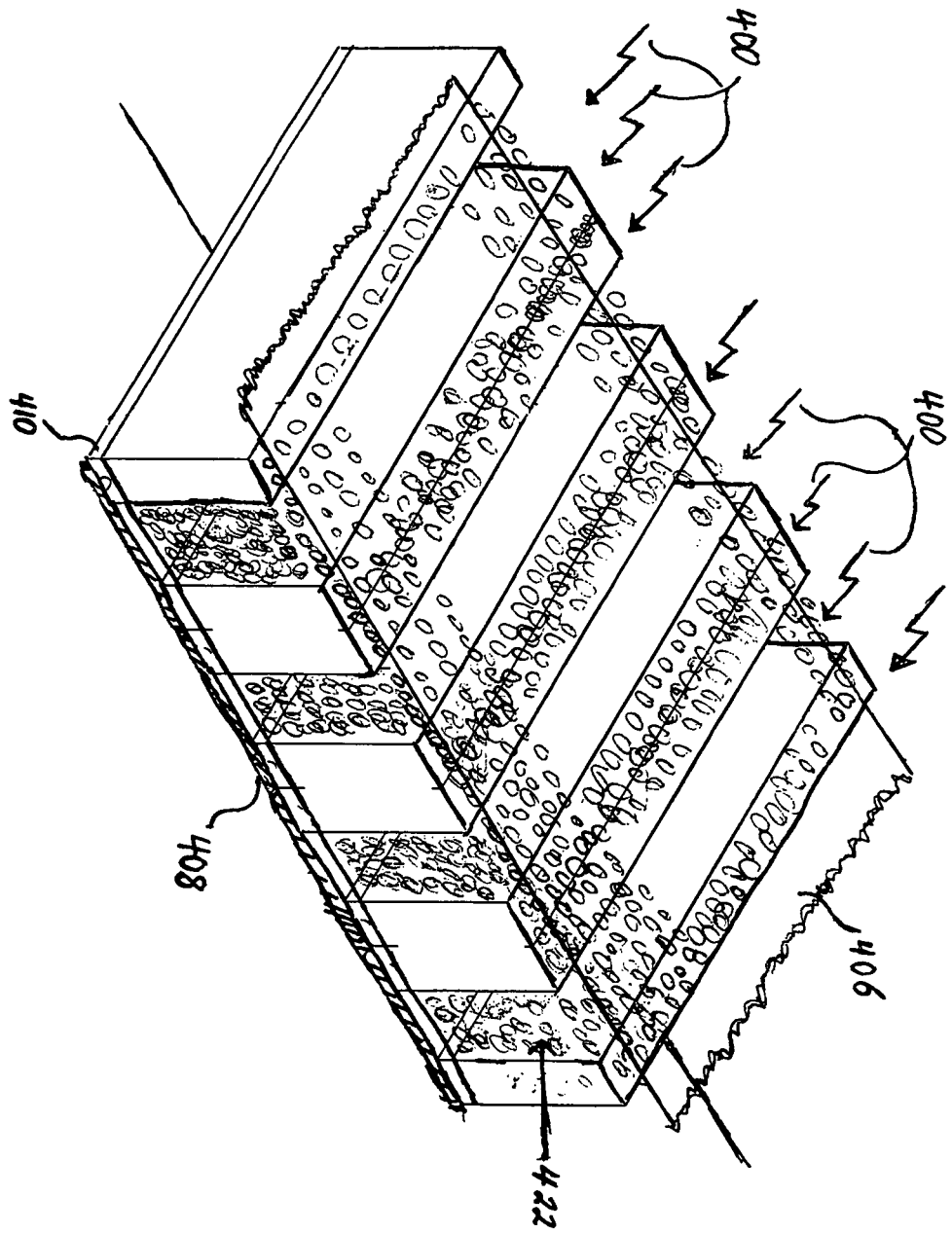
FIG. 6 illustrates a perspective view of a structured quantum dot detector with trench cells positioned in an edge-on geometry appropriate for slit scan x-ray radiography in which radiation is incident parallel to the long axis of the trench.

The implementation of an edge-on detector geometry permits a degree of flexibility in the choice of cell shape and cell dimensions. FIG. 5 illustrates a perspective view of a structured quantum dot detector with trench cells wherein each trench is comprised of a continuous cathode 306 matched with structured anodes 308. The base or substrate 310 supplies power to the detector and incorporates appropriate readout electrons such that output data can be saved to a computer or made available for display. The quantum dots that fill the trenches are not shown. The structured cell quantum dot detector with trench cells is shown with radiation 300 incident in an edge-on geometry appropriate for slit scan radiography. In addition to any energy resolution provided by the readout electronics there is also limited energy resolution inherent in this geometry since the beam spectrum changes as the beam passes through successive trenches. Furthermore this geometry can be used to reduce the event count per detector element. Note that in Nuclear Medicine this detector design provides depth of interaction information. (Another option is to employ this structured quantum dot detector with trench cells in a face-on position if the face-on geometry offers adequate detection efficiency.) The edge-on structured cell quantum dot detector represents an alternative to the edge-on scintillator detectors described by Nelson (Nelson R, U.S. Pat. No. 8,017,906, Sep. 13, 2011) as well as to edge-on semiconductor detectors. The readout systems and features described by Nelson can be employed with the structured quantum dot detector with trench cells. A second edge-on detector geometry as shown in FIG. 6 can be implemented, based on FIG. 5, in which the radiation is incident parallel to the long axis of the trenches. Once again depth of interaction information (as well as limited energy resolution) is available due to the structured anodes 308. Readout electronics can be used to provide photon counting or spectroscopy capability. If depth of interaction information or a reduced event count rate per pixel is not of concern then the detector design can be simplified so that the trenches are continuous (unstructured). One implementation positions the readout anode (if the anode is preferred for readout) and cathode at the two ends of the continuous trench. This enables relatively small readout anodes but potentially long transmission paths for some of the radiation-generated signals. An alternative implementation is to position the readout anode and cathode on the top and bottom surfaces of the continuous trenches as shown in FIG. 6. FIG. 6 shows radiation 400 incident parallel to the long axis of the trenches with readout anode 408 metal contact below the silicon base or substrate 410 and cathode 406 metal contact above the quantum dots 422 that fill the continuous trenches. The trenches still assume the role of the etched silicon pores that comprise the structured cell used in porous silicon quantum dot radiation detectors but the detected charges now travel a distance comparable to the depth of the trench and silicon base rather than the long axis of the trench. Furthermore, as with conventional structured cell detectors, the continuous strip anodes (for example) can always be segmented. In an edge-on detector geometry this restores the depth-of interaction capability and reduced count rate per pixel but at a cost of more readout elements. Although the trenches shown in FIGS. 5 and 6 are parallel it is relative straightforward to form a trench geometry (as well as an anode geometry) that diverges from the radiation entrance surface to compensate for the (typical) diverging nature of most x-ray sources (Nelson R, U.S. Pat. No. 4,937,453, Jun. 26, 1990). Within operational limits the widths of the trench channels can be made to diverge as an alternative to a configuration in which the diverging trenches are of identical width. The readout anode and cathode shapes need to match the requirements of the geometry of the trenches. For example, if the anode is positioned on the top surface and the trenches diverge from the radiation entrance surface then an anode metal contact strip must cover the appropriate set of trenches that define a detector element. In those instances in which the divergence is gradual then focused, rectangular anode strips that follow the divergence may be an acceptable substitute for focused, diverging anode strips. The ability to match the divergence of the x-ray source with a focused detector is useful for slit scanning and slot scanning (including fan beam and cone beam CT scanning). A diverging readout anode design can also be implemented with structured cell, conventional porous or etched silicon quantum dot radiation detectors when used as edge-on detectors. Various cell shapes can be implemented and the 2-D distribution of cells can be selected to conform to the divergence of the readout anodes if advantageous. Furthermore, although the edge-on geometries in FIGS. 4-6 show a flat entrance surface, the entrance surface can be contoured if an application benefits significantly from this modification. If the depth of a cell represents a limitation in the edge-on orientation then a method of effectively extending the cell depth is to butt two cathode surfaces of two edge-on detectors together so that the cell depth is almost doubled. Essentially this creates an array with two rows of active detectors. Cost-savings can be introduced if the signals from the corresponding detector elements in the two rows are combined before being readout. This merging of signals may be reasonable for some applications such as slit scanning whereas separate readouts may be desirable for TDI (time delay integration) slot scanning (or CT scanning). Butting edge-on detectors to increase the density of the active detector volume has been described in previous patents (Nelson R, U.S. Pat. No. 4,937,453, Jun. 26, 1990). Since slot scanning (continuous motion or discrete stepped motion) requires 2-D arrays of detectors in general, for coded aperture PCI the pre-object mask and the pre-detector mask will be movable unless separate sets of slots are used for the two acquisition modes. Although continuous 2-D arrays of detectors are often employed for slot scanning (including fan beam and cone beam CT scanning), a 2-D array detector can be approximated by an array of 1-D edge-on detectors in close proximity (Nelson R, U.S. Pat. No. 4,937,453, Jun. 26, 1990).

The structured cell quantum dot detectors shown in FIGS. 4, 5 and 6 (as well as other versions that use alternative materials such as amorphous or polycrystalline semiconductors) and other structured detectors such as 3-D semiconductor (such as silicon) detectors are also suitable for human and small animal CT and Nuclear medicine imaging (including probes and Compton cameras) and PET imaging since they offer high spatial resolution, good-to-excellent timing resolution, and good-to-very good energy resolution. Imaging with ionizing radiation such as, but not exclusively, x-rays or gamma rays for any of PCI, CT, tomosynthesis, slit scan, slot scan, area (such as chest, breast, etc.), Nuclear medicine, PET, Compton, probe and scatter imaging, etc. represent implementations of diagnostic ionizing radiation imaging. As mentioned earlier, readout elements in an edge-on orientation can be segmented to provide 2-D detection capability which could be used for depth of interaction detection determination (or sub-aperture resolution). Costs can be reduced by implementing versions of these structured quantum dot detectors that implement weighted readouts based on contributions from the detected signals of multiple detector elements shared between two readout elements at the ends of strip detector (1-D resolution) or four readout elements at the corners of an area detector (2-D resolution). Furthermore the continuous trench cells of FIG. 6 can be implemented as long trench cell with a readout element at either end. A related approach, which lacks energy resolution but scales to much longer lengths, uses lead straws with readout elements at both ends (see Nelson R, U.S. Pat. No. 8,017,906, Sep. 13, 2011). In addition, the structured cell quantum dot edge-on detectors can be butted together to increase the density of the active detector volume (Nelson R, U.S. Pat. No. 4,937,453, Jun. 26, 1990). If the weighted readout electronics are sufficiently fast then sub-aperture resolution (SAR) can be implemented for slit and slot scanning (and CT scanning) applications using structured detectors (Nelson R, U.S. Pat. No. 6,583,420, Jun. 24, 2003; Nelson R, U.S. Pat. No. 7,291,841, Nov. 6, 2007; Nelson R, U.S. Pat. No. 7,635,848, Dec. 22, 2009 and Divisional. U.S. Pat. No. 8,115,174 B2, Feb. 14, 2012, Divisional. U.S. Pat. No. 8,115,175 B2, Feb. 14, 2012, Divisional. U.S. Pat. No. 8,183,533 B2, May 22, 2012; Nelson R, U.S. Pat. No. 8,017,906, Sep. 13, 2011 Nelson R, U.S. Patent Provisional Application No. 61/689,139, May 31, 2012).

Attenuation imaging and PCI slit and slot scanning have been described in conjunction with dedicated 1-D or 2-D small-area detectors. The same scanning techniques can be implemented with 2-D storage phosphor plate detectors and other 2-D array detectors, comprising dual-use slit and slot scanning systems that employ area detectors. For example, the 1-D pre-detector and pre-object masks, pre-object slits that overlap with pre-detector slits, or a combination of both can be implemented for slit scan PCI. The advantage of inherent scatter reduction is available in both attenuation imaging and PCI modes for these 2-D detectors. Multiple sets of slits or slots can be employed to increase x-ray source utilization efficiency.

Although applications discussed herein are primarily directed at medical, industrial, and scientific x-ray (and in some cases gamma ray) imaging applications, in principle the invention can also be used with other types of particles, including those that can exhibit phase shift effects (for example neutrons). In addition the invention can be used with established interferometric techniques such as grating-based differential phase contrast imaging. Furthermore, the formulations for the described x-ray radiation detectors (storage phosphor plates, structured cell quantum dot detectors, etc.) can be altered to improve the detection efficiency for these particles.

THE INVENTION LITERATURE REFERENCES EXPRESSLY INCORPORATED BY REFERENCE

Nelson R, Barbaric Z, High Efficiency X-Radiation Converters, U.S. Pat. No. 4,560,882, [Dec. 24, 1985]
Nelson R, X-ray Detector for Radiographic Imaging, U.S. Pat. No. 4,937,453 [Jun. 26, 1990].
Nelson R, et al., Apparatus for Narrow Bandwidth and Multiple Energy X-ray Imaging, U.S. Pat. No. 4,969,175 [Nov. 6, 1990].
Nelson R, Nelson W, Device and System for Improved Imaging in Nuclear Medicine and Mammography, U.S. Pat. No. 6,583,420 [Jun. 24, 2003].
Nelson R, Nelson W, Device and System for Enhanced SPECT, PET, and Compton Scatter Imaging in Nuclear Medicine, U.S. Pat. No. 7,291,841 [Nov. 6, 2007].
Nelson R, Edge-on SAR Scintillator Devices and Systems For Enhanced SPECT, PET and Compton Gamma Cameras, U.S. Pat. No. 7,635,848 [Dec. 22, 2009] and Divisional U.S. Pat. No. 8,115,174 B2 [Feb. 14, 2012], Divisional U.S. Pat. No. 8,115,175 B2 [Feb. 14, 2012], Divisional U.S. Pat. No. 8,183,533 B2 [May 22, 2012].
Nelson R, Nelson W, Slit and Slot Scan, SAR, and Compton Devices and Systems for Radiation Imaging, U.S. Pat. No. 8,017,906 [Sep. 13, 2011].
Nelson R, Nelson W, High Resolution Imaging System for Digital Dentistry, U.S. patent application Ser. No. 12/930, 771. Filing date: Jan. 18, 2011.
Nelson R, Nelson W, Compton Camera Detector Systems for Integrated Compton-PET and CT-Compton-PET Radiation Imaging, U.S. Patent Provisional Application No. 61/689,139, May 31, 2012 Campbell I, Crone B, Quantum-Dot/Organic Semiconductor Composites for Radiation Detection, Advanced Materials vol. 18 (1), p. 77-79, 2006.
Da Via C, Parker S, et al., Dual readout-strip/pixel systems, Nucl. Instru. Meth. A, vol. 594, p. 7-12, 2008.
Johnson J, Schweizer S, Lubinsky A, A Glass-Ceramic Plate for Mammography, J. Am. Ceram. Soc. Vol. 90, no. 3, p. 693-698, 2007.
Keyrilainen J, Bravin A, et al. Phase-Contrast X-ray Imaging of Breast, Acta Radiologica vol. 8, p. 866-884, 2010.
Morita T, Yamada M, et al., A Comparison between Film-Screen Mammography and Full-Field Digital Mammography Utilizing Phase Contrast Technology in Breast Cancer Screening Programs, Lecture Notes in Computer Science, 5116, p. 48-54, 2008
Munro P, Ignatyev K, Speller R, Oliva A, Design of a Novel Phase Contrast Imaging System for Mammography, Phys. Med. Biol., vol. 55, p. 4169-4185, 2010.
Oliva A, Ignatyev K, Munro P, Speller R, Design and Realization of a Coded-Aperture Based X-ray Phase Contrast Imaging for Homeland Security Applications, Nucl. Instru. Meth. A, vol. 610, p. 604-614, 2009.
Rowlands J, The Physics of Computed Radiography, Phys. Med. Biol., vol. 47, R123-R166, 2002.
Urdaneta M, Stepanov P, Weinberg I, et al., Porous Silicon-Based Quantum Dot Radiation Detector, 2010 International Workshop on Radiation Imaging Detectors.
Urdaneta M, Stepanov P, Weinberg I, et al., Quantum Dot Composite Radiation Detector, oral presentation, 2010 IEEE Nuclear Science Symposium.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A dual-use imaging slit or slot scan system for simultaneous PCI and conventional digital imaging of the same object, wherein the system is comprised of:
   At least one radiation source,
   At least one set of pre-object and pre-detector slits or slots for conventional digital imaging,
   At least one set of pre-object and pre-detector slits or slots for PCI digital imaging,
   A set of pre-object and pre-detector masks associated with each set of pre-object and pre-detector slits or slots for PCI digital imaging,
   A radiation detector employed with each pre-detector slit or slot,
   Detector readout electronics configured for analyzing the readout signals using energy integration or photon counting or energy resolution techniques, and
   An electronic communications link to a computer for data post-processing, storage, and display.

2. A radiation detector system for diagnostic ionizing radiation imaging comprising: at least one edge-on 3-D electrode semiconductor detector or edge-on cell semiconductor detector filled with semiconductor quantum dots or polycrystalline semiconductor or amorphous semiconductor material for radiation detection; detector readout electronics configured for timing resolution and analyzing the readout signals using energy integration or photon counting or energy resolution techniques; and an electronic communication link to a computer for data processing, storage and display.

3. The radiation detector system of claim 2, wherein the edge-on cell semiconductor detector implements a trench cell shape filled with semiconductor quantum dots or polycrystalline semiconductor or amorphous semiconductor material.

4. The edge-on cell semiconductor detector of claim 3, wherein the trench cell is a continuous trench cell or a structured trench cell.

5. The radiation detector system of claim 2, wherein the at least one edge-on 3-D electrode semiconductor detector or edge-on cell semiconductor detector is a focused, edge-on 3-D electrode semiconductor detector or a focused, edge-on cell semiconductor detector implementing rectangular or diverging readout strips that follow the divergence of the radiation source.

6. The radiation detector system of claim 2, wherein the radiation detector system is employed for slit scanning, slot scanning, CT scanning, tomosynthesis, area, scatter, PCI, Nuclear Medicine, PET, Compton camera, and radiation probe imaging.

7. The radiation detector system of claim 2, wherein the at least one edge-on 3-D electrode semiconductor detector or edge-on cell semiconductor detector implements a weighted readout based on the detected signals of multiple detector elements shared between two readout elements at the ends of a strip detector or four readout elements at the corners of an area detector.

* * * * *